(12) United States Patent
Copeland et al.

(10) Patent No.: US 6,429,008 B1
(45) Date of Patent: *Aug. 6, 2002

(54) APPARATUS AND METHOD FOR GROWING ANAEROBIC MICROORGANISMS

(75) Inventors: James C. Copeland, Ashland, OH (US); Howard I. Adler, deceased, late of Oak Ridge, by Martha Vogeler Adler, executrix; Gerald E. Spady, Oak Ridge, both of TN (US)

(73) Assignee: Oxyrase, Inc., Mansfield, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/812,204

(22) Filed: Mar. 19, 2001

Related U.S. Application Data

(63) Continuation of application No. 09/321,812, filed on May 28, 1999, now Pat. No. 6,204,051, which is a continuation-in-part of application No. 08/963,664, filed on Nov. 3, 1997, now Pat. No. 5,955,344, which is a continuation of application No. 08/237,773, filed on May 4, 1994, now Pat. No. 5,830,746.

(51) Int. Cl.[7] .............................................. C12M 1/00
(52) U.S. Cl. .............................. 435/303.2; 435/305.4; 435/307.1; 435/801; 422/102
(58) Field of Search ........................... 435/288.3, 303.2, 435/305.4, 307.1, 801; 422/102

(56) References Cited

U.S. PATENT DOCUMENTS

| | | | | |
|---|---|---|---|---|
| 2,348,448 A | * | 5/1944 | Brewer | |
| 5,830,746 A | * | 11/1998 | Copeland et al. | 435/243 |
| 5,955,344 A | * | 9/1999 | Copeland et al. | 435/243 |
| 6,204,051 B1 | * | 3/2001 | Copeland et al. | 435/305.4 |

* cited by examiner

Primary Examiner—David A. Redding
(74) Attorney, Agent, or Firm—Fay, Sharpe, Fagan, Minnich & McKee LLP

(57) ABSTRACT

An apparatus for growing anaerobic microorganisms is provided having a dish top that contains a sealing ring upon which the media surface in the dish bottom rests when the apparatus is inverted. The contact between the sealing ring and the media surface forms a seal that traps the gas in the headspace between the media surface and the inside of the dish top. A oxygen reducing agent can also be incorporated into the media together, in some instances, with a substrate which react with oxygen in the media and with oxygen in the headspace thereby creating an environment suitable for growing anaerobic, microaerophilic and facultative anaerobic microorganisms.

22 Claims, 8 Drawing Sheets

APPARATUS AND METHOD FOR GROWING ANAEROBIC MICROORGANISMS

CROSS REFERENCE TO RELATED APPLICATIONS

This application is a continuation application of Ser. No. 09/321,812, filed May 28, 1999, now U.S. Pat. No. 6,204,051, issued Mar. 20, 2001, which is a continuation-in-part application of Ser. No. 08/963,664, filed Nov. 3, 1997, now U.S. Pat. No. 5,955,344, issued Sep. 21, 1999, which is a continuation application of Ser. No. 08/237,773, filed May 4, 1994, now U.S. Pat. No. 5,830,746, issued Nov. 3, 1998.

BACKGROUND OF THE INVENTION

1. Field of Invention

The present invention relates to an apparatus and method for growing anaerobic microorganisms. The apparatus is comprised of a specially designed culture dish which can be reconfigured such as by inverting the dish to produce an anaerobic environment. An oxygen reducing agent such as a biocatalytic oxygen reducing agent can also be incorporated into the media present in the apparatus together, in some circumstances, with a substrate. The biocatalytic oxygen reducing agent and the substrate present in the media react with oxygen enclosed in the culture dish to create an environment suitable for growing and maintaining anaerobic microorganisms.

2. Description of Prior Art

Microorganisms are important to our well being. This is evident in health care, agriculture and industry. To be able to simply and quickly isolate and grow microbes is economically important. For example, being able to quickly and specifically isolate and identify a microbe responsible for infection is important in the human health care field. This basic technique is also important in the agriculture industry. Large scale processing of food requires constant microbial monitoring. The speed and efficiency at which this can be done determines the length of time finished food products must be held in storage before they can be distributed for sale.

Control of the environment is necessary for control of microbial growth. In particular, control of oxygen content in the immediate environment is crucial for microbial growth. Microorganisms can be divided into groups based on their need for, and tolerance of, oxygen. There are those that require oxygen to grow. These are "aerobes". Some microorganisms are able to grow with or without oxygen. These are "facultative anaerobes". Another group of microorganisms can grow only in the presence of very low levels of oxygen. These are the "microaerophiles". Finally, some microorganisms can not tolerate oxygen. They are inhibited by it or may be killed by it. These are the "anaerobes".

This fundamental property of microorganisms, that is their ability to grow in or tolerate oxygen, is used daily to isolate, grow, and manipulate them. One basic technique in microbiology, is the plating method. This generally involves the use of a dish, developed by Petri (i.e. "Petri dish") in 1880's, and solidified (agar or gelatin-based) medium.

A Petri dish is usually a round, shallow, flat-bottomed, glass or plastic dish (often e.g. 10 cm diameter) with a vertical side, that cooperates with a similar, slightly larger structure which forms a loosely-fitting lid. Petri dishes are used in microbiology, e.g., for the preparation of plates.

The purpose of the Petri dish is to provide a controlled environment for selectively growing microbes. The dish is sterilized and designed to maintain a sterile environment inside while freely exchanging gases, normally air, with the outside environment.

The medium utilized in conjunction with the Petri dish can be formulated to provide a necessary and selective environment for a specific microorganism. Solid medium in a Petri dish can be prepared using aseptic technique by pouring sterile molten or liquid (agar- or gelatin-based) medium into a Petri dish to a depth of 3–5 mm and allowing it to set. Generally, freshly poured plates to be used for separation and/or generation of microbes should be left for 30 minutes in a 45° C. hot-air incubator with the lid partly off so that the surface moisture can evaporate. Such "drying" before inoculation prevents unwanted spreading of the inoculum in the surface film of the moisture.

The solid medium surface inside the dish provides a place to grow microorganisms. By inoculating (or "plating") the surface of the agar in a controlled way (i.e. "streaking"), single colonies of a microorganism can be obtained. With this technique the microbiologist can separate microbes one from another. Isolation and purification is mandatory to further characterization and study. Using this dish design, a microbiologist can isolate and grow the great majority of microorganisms known today.

Working with microbes that are microaerophiles or anaerobes poses a problem. The culture dishes for these microbes must be incubated in a controlled gaseous environment that lacks oxygen, or at least most of the oxygen, found in air. This is done by placing the culture or Petri dish containing medium inside a container that is sealed from the outside atmosphere. For one or a few dishes, a sealable bag or jar (i.e., "Brewer Jar") is used (Becton Dickinson Microbiology Systems, 1994 Catalog, p 89–p 94). In this case, chemicals and a catalyst (see U.S. Pat. No. 4,287,306 issued Sep. 1, 1982 to Brewer entitled "Apparatus for Generation of Anaerobic Atmosphere") are placed inside the container that, when activated chemically, reacts with the oxygen in the container, thus removing it. The catalyst is necessary to bring about the reaction at low temperatures in a short time.

In addition, for many culture dishes, a sealed table-top chamber can be used (Anaerobe Systems, San Jose, Calif.). This chamber is evacuated and flushed with inert gases, such as nitrogen and/or carbon dioxide. Sometimes chemicals and a catalyst are used to consume the oxygen inside the chamber and fresh, inert gas is supplied as needed. The microbiologist works with the culture dishes inside of this chamber through ports fitted with gloves. A means is provided for introducing materials into and taking items out of the chamber without breaching the anaerobic environment inside.

Work with microaerophiles and anaerobes under these conditions is labor intensive, difficult, expensive, and time consuming. The microbiologist is often frustrated by having to wait for the slowest growing microbe in order to retrieve all culture dishes from a bag or jar since once the bag or jar is opened, the microbes are exposed to oxygen. A failure in the system can be catastrophic for all of the microbial isolates inside.

To overcome many of these problems (see U.S. Pat. No. 2,348,448 issued May 9, 1944 to Brewer entitled "Apparatus for the Cultivation of Anaerobic and Microaerophilic Organisms") Brewer developed a culture dish lid (i.e., "Brewer Lid") that formed a seal between a ring inside the lid with the agar or gelatin-based surface. Within the dish, a very small, defined headspace is formed by the lid and the agar surface. An anaerobic environment is created inside this trapped headspace by reacting oxygen with chemical reducing agents, such as thioglycollate, incorporated in the medium. The limited volume of the headspace is important to the function of the Brewer Lid.

However, a number of drawbacks exist in the use of the Brewer Lid. The capacity and the rate for oxygen removal is limited by the sensitivity of the microorganism to the chemical reducing agent in the medium (see "Mechanism of Growth Inhibitory Effect of cysteine on *Escherichia coli*." of Kari, et al., *J. Gen. Microbiol.*, 68, 1971, p. 349 and "Methods for General and Molecular Bacteriology", Editor: Gerherdt, American Society for Microbiology, 1994, p. 146.). Moreover, the lid is made of heavy glass and is expensive. It is available today (Kimble Glass Company, Vineland, N.J.), but is not widely used because of serious limitations that include cost, handling difficulties, and poor response of anaerobic microorganisms.

Another limitation is caused by the material of construction. The glass Brewer Lid is made very heavy to insure a good seal between the ring inside the Brewer Lid and the agar surface. Cultures dish bottoms fitted with the heavy Brewer Lid are not easy to handle or to move about. They can not be stacked inside an incubator. Thus, precious incubator space is wasted. Stacked dishes crush the agar medium of the lowest dishes in the stack, because of the weight of the dishes above them. This causes the headspace above the agar to collapse resulting in contact between the inside of the Brewer Lid and the agar surface. When this happens, the microbial growth on the surface is spread out and separation of individual colonies is lost. Motile microbes will migrate and further frustrate separation.

Because of their weight and material of construction, Brewer Lids do not lend themselves to commercial production of pre-made agar or gelatin-based plates. The commercial process requires assembly line filling of the dishes, packaging the filled dishes in stacks, and handling and storing these dishes. Pre-made agar plates are widely used in clinical microbiological laboratories. This limitation of the Brewer Lid is economically significant.

The headspace inside the Brewer Lid formed by the lid and agar surface is very small. This limited headspace is determined by the ability of the chemical reducing agent ($H_2S$, cysteine, thioglycollate, etc.) to reduce oxygen in the headspace. The amount of chemical reducing agent used in the medium in turn is constrained by anaerobic microorganism's sensitivity to it. The sum of these limitations is a very small head space that imparts severe problems to the function of the Brewer Lid for its intended purpose, i.e. to grow anaerobic and microaerophilic microorganisms.

Another limitation of the Brewer Lid is that the very limited head space can not hold much moisture. Fresh agar medium is generally greater than 98 percent water. Upon incubation, water in the medium evaporates and condenses upon the upper surface of the inside of the lid. This condensate can become sufficient to fall to the agar surface and to flood it. Under such conditions, the plate is ruined and can not be used for isolation and purification of the microbe.

The very limited headspace imposes still more limitations on the Brewer Lid. No provision is made to incorporate $CO_2$ into the headspace above the agar surface. This is important for the rapid growth of some microorganisms and may be required by others. Yet this feature should be made optional for the microbiologist, because for some uses of the culture dish the microbiologist may not want to include $CO_2$ in the headspace. Reports show that $CO_2$ can change the pH of the medium it contacts. This in turn can interfere with the determination of susceptibility to some antibiotics (see "Effect of $CO_2$ on Susceptibilities of Anaerobes to Erythromycin, Azithromycin, Clarithromycin, and Roxithromycin", Spangler, et al., *Antimicrob. Agents Chemotherapy*, 38, p. 20, 1994). Since $CO_2$ is generated in anaerobic jars and bags by commercial catalysts products, this problem is commonly encountered. $CO_2$ is a component of the gas used to flush anaerobic chambers and incubators too.

Another desired feature for a self contained culture dish is an indicator to show that the headspace is anaerobic. These features are difficult to impossible to include in the Brewer Lid because of the very small space between inside the lid top and the agar surface.

Several attempts have been made to design a culture dish that provides a self-contained environment for growing anaerobic microorganisms (see U.S. Pat. No. 2,701,229 issued Feb. 1, 1955 to Scherr entitled "Apparatus for the Cultivation of Microorganisms"; U.S. Pat. No. 3,165,450 issued Jan. 12, 1965 to Scheidt entitled "Anaerobic Culturing Device"; U.S. Pat. No. 4,294,924 issued Oct. 13, 1981 to Pepicelli, et al. entitled "Method and Container for Growth of Anaerobic Microorganisms"; U.S. Pat. No. 4,299,921 issued Nov. 10, 1981 to Youssef entitled "Prolonged Incubation Microbiological Apparatus and Filter Gaskets Thereof"; and U.S. Pat. No. 4,859,586 issued Aug. 8, 1989 to Eisenberg entitled "Device for Cultivating Bacteria"). The fact that the Brewer Lid and none of these inventions are commonly or commercially available or used widely by microbiologists today, attest to their limitations and shortcomings. The need to simplify and reduce the cost for isolating and growing anaerobic and microaerophilic microorganisms still exists today.

It is therefore an object of the present invention to provide an improved apparatus and method for cultivating and/or enumerating anaerobic microorganisms which obviate the above-mentioned disadvantages of the prior art.

Another object of the present invention is to provide an improved anaerobic culturing apparatus which is extremely simple, inexpensive and easy to use and wherein the proper anaerobic environment is produced and maintained in an extremely efficient manner.

These and other additional objects and advantages of the present invention will become apparent from the following description of the invention.

SUMMARY OF THE INVENTION

The present inventors have designed a novel culture apparatus or dish in order to eliminate many of the difficulties observed in the prior art. It has been found that the use of the new culture dish (i.e., "OxyDish™") together with an oxygen reducing agent (preferably a biocatalytic oxygen reducing agent) and, in some instances, a substrate, produces a controlled, self-contained environment for isolating, enumerating, identifying and growing facultative aerobes, microaerophiles and anaerobes. The use of the specially designed culture dish along with an oxygen reducing agent makes possible the design and function of a culture dish that utilizes some features of the Brewer Lid, but overcomes its limitations and makes possible novel and improved characteristics.

In this regard, the present invention is directed to a specifically designed culture dish with a dish top or cover that contains a sealing ring on the inside upon which the solid media surface in the bottom dish rests when the dish is inverted to form a media-ring seal. The seal so formed traps the gas in the headspace between the media surface and the inside of the dish top or cover. In addition, an oxygen reducing agent, such as a biocatalytic oxygen reducing agent, can be incorporated into the media present in the culture dish together, in some instances, with a substrate which reacts with oxygen in the media and the headspace to create an environment suitable for growing anaerobic microorganisms.

The preferred biocatalytic oxygen reducing agent (see "A Novel Approach to the Growth of Anaerobic Microorganisms" of Adler, et al., *Biotechnol. Bioegn. Symp.* 11, J. Wiley & Sons, New York, 1981, p. 533 and U.S. Pat. No. 4,476,224 issued Oct. 9, 1984 to Adler entitled "Material and Method for Promoting the Growth of Anaerobic Bacteria") utilized in the invention is comprised of oxygen scavenging membrane fragments which contain an electron transport system which reduces oxygen to water in the presence of a hydrogen donor. These oxygen scavenging membrane fragments can be derived from the cytoplasmic membranes of bacteria (U.S. Pat. No. 4,476,224) and/or from the membranes of mitochondrial organelles of a large number of higher non-bacterial organisms. Other known biocatalytic oxygen reducing agents such as glucose oxidase, alcohol oxidase, etc. can also be utilized.

The biocatalytic oxygen reducing agents suitable for use in the invention are non-toxic to microorganisms. Being catalysts, they are dynamic and highly efficient at reducing the oxygen in the trapped headspace in the specially designed culture dish. The biocatalytic oxygen reducing agents use substrates that are commonly found in microbiological media and that are natural to microorganisms to effect this reaction. The products produced from this reaction are also natural and non-toxic to microorganisms. The use of the biocatalytic oxygen reducing agents makes possible the opening and closing of this dish several times and the agents continue to reduce the oxygen trapped in the headspace after each occurrence.

The culture dish ("OxyDish™") containing the oxygen reducing agent provides a means to work with microorganisms free of the complications and expense of anaerobic bags, jars, incubators, or chambers. Each dish is light in weight and is designed to be stacked without crushing the solid (agar or gelatin-based) medium in the lower dishes in the stack. The dishes can be made of low cost materials, preferably plastic, are designed to be readily molded, are sterilizable, and preferably can be disposed after use. Because of the incorporation of a biocatalytic means of removing oxygen, an enlarged headspace is possible. This enlarged headspace relieves the moisture condensation problems encountered with the Brewer Lid.

Moreover, the dish top of the culture dish in certain embodiments of the present invention, has a small dome or cavity designed to contain an anaerobic gas (such as $CO_2$) generating pad or indicator strips to show the anaerobic state within the headspace of the closed culture dish. A variation of this dish design provides for additional removal of moisture from the dish as needed by placing pores in the bottom of the dish base. This feature prevents the build-up of excess condensate inside the dish which leads to flooding of the agar media surface. The pores are too small to let molten agar media flow out of the dish, yet they provide an exit for moisture. An oxygen intruding into the dish through these pores must pass through the media containing the oxygen reducing agent. This intruding oxygen is removed before it can diffuse to the top layer of media or into the headspace where it would interfere with growth of anaerobic microorganisms.

The culture dish, i.e., "OxyDish™" of the present invention, is designed for automated preparation of agar or gelatin-based media plates necessary for commercial production. When in the upright position, the dish can be readily filled with molten medium (such as a molten agar or gelatin-based media) without the sealing ring contacting the medium surface. When stored or used, the dish is placed into an inverted position. In this position, a seal (i.e. a media-ring seal) is formed by the contact of the sealing ring of the dish top with the media surface contained in the dish bottom when the media surface comes to rest on the sealing ring. This creates a headspace defined by the media surface, the inside wall of the sealing ring, and the inside top of the dish lid.

Furthermore, when the culture dish is utilized with the oxygen reducing agent such as a biocatalytic oxygen reducing agent, the oxygen reducing agent in the media reacts with the oxygen trapped in that headspace. This reaction renders the headspace sufficiently low in oxygen such that microorganisms affected by the presence of oxygen can grow on the media surface typically within 24 to 48 hours when the dish is incubated at 35° C. to 37° C. in an aerobic incubator. Any oxygen that intrudes into the dish around the media ring-seal or through the plastic is removed by the action of the reducing agent. The catalytic reducing agent facilitates the design and function of this dish.

The media suitable for use in the present invention includes any solid type media which can be inverted to form a media ring-seal. Solid media generally consists of liquid media which have been solidified ("gelled") with an agent such as agar or gelatin. Examples of other known suitable gelling agents include alginate, gellan gum ("Gelrite™") and silica gel ("Pluronic Polyol F127™"). The solid type media is of such a composition to support growth of anaerobes, microaerophiles and facultative aerobes.

Further, the culture dish, i.e., "OxyDish™", of the present invention, is designed in certain embodiments so that it can be stacked in a stable configuration. The dish top has a stacking ring that interlocks with the adjacent dish top below it. The dish bottom, when the assembled dish is inverted and placed in a sealed position, rests (i.e., nests) between the two adjacent dish tops. The functionality of the dish to establish and maintain an anaerobic environment is preserved and protected in the stack. The stackability of the culture dish increases the efficient use of incubator space. Stackability is also important for the mechanized filling of these dishes and shipment of dishes or of finished pre-made, plates to the microbiologist or end user.

The culture dish of the present invention, simplifies handling anaerobes by the microbiologist or laboratory technician. The culture dish, i.e., "OxyDish™", can be opened and closed several times while continuing to generate an anaerobic environment in the closed position. The specially designed culture dish significantly increases the microbiologist's efficiency by reducing and simplifying the number of manipulations required to work with anaerobes. Furthermore, the microbiologist can now treat each culture dish and its microbial contents individually. This allows the microbiologist to make decisions based on his observations of each isolate or treatment, rather than having to wait for the slowest growing isolate in a group of culture dishes present in a sealable jar, bag, etc. In addition, the self-contained, environmentally controlled culture dish provides a secure environment for the microbe inside.

The foregoing has outlined some of the most pertinent objects of the invention. These objects should be construed to be merely illustrative of some of the more prominent features and applications of the intended invention. Many other beneficial results can be attained by applying the disclosed invention in a different manner or by modifying the invention within the scope of the disclosure. Accordingly, other objects and a more detailed understanding of the invention may be had by referring to the drawings, the detailed description of the invention and the claims which follow below.

BRIEF DESCRIPTION OF THE DRAWINGS

The following is a brief description of the drawings which are presented for the purposes of illustrating the invention and not for purposes of limiting the same.

DETAILED DESCRIPTION OF THE INVENTION

Figure 2:
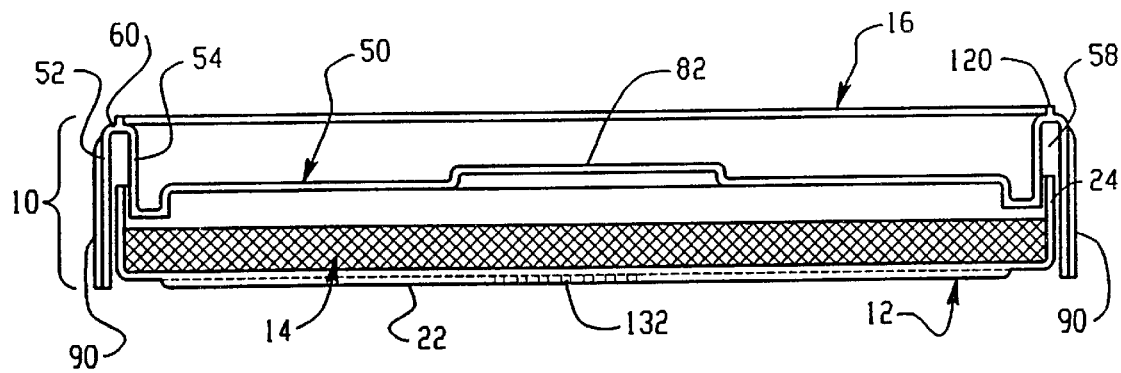
FIG. 2 is a cross-sectional view of the assembled culture dish of FIG. 1 shown in what is generally referred to as a first or upright position.

The culture dish of the present invention is designed to meet the strict requirements of anaerobiosis while simplifying handling by the microbiologist. As shown in the drawings, a culture dish 10 includes two separately configured parts. A first component or dish bottom 12 receives a culture media 14 and a dish cover or top 16 defines a second component of the culture dish. The dish bottom and dish top selectively cooperate to define a culture dish for growing microorganisms. Together, the dish bottom 12 and dish cover 16 define in a first position or orientation a covered Petri culture dish as shown in FIG. 2. This first position will be referred to as an upright position. When inverted (FIG. 3), the dish bottom and dish cover alter their cooperative configuration to define a second position or orientation that forms an enclosed chamber or head space 80 in which anaerobic microorganisms 20 can be cultivated.

Figure 1:
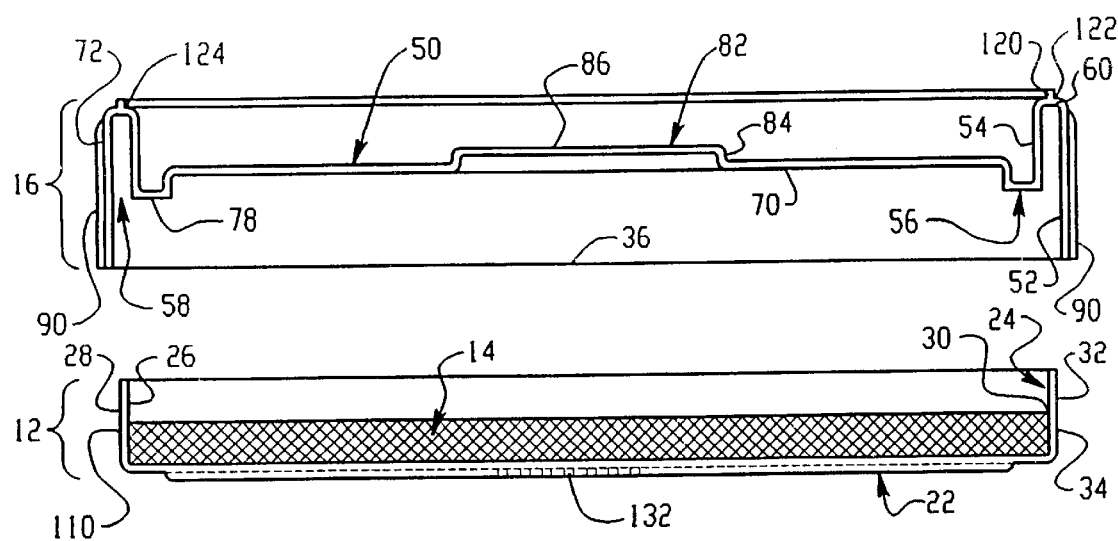
FIG. 1 is a cross-sectional view of a two-part culture dish for growing anaerobic microorganisms shown in separated or exploded relation.

The structural and functional details of the dish bottom 12 will be described with reference to FIGS. 1–3, and more particularly with reference to FIGS. 4A–4D. The dish bottom is comprised of a generally planar base 22 and a circumferentially continuous side wall 24 extending generally orthogonally from the base. For purposes of discussion only, the side wall will be described as extending upwardly from the base as illustrated in FIGS. 1, 2, and 4. It will be recognized, however, that any directional description is merely for purposes of simplifying an understanding of the present invention.

In addition, the dish bottom 12 has a first or inner surface 26 that faces inwardly over the base and side wall toward the cavity defined by the cup-shaped arrangement of the base and side wall. Likewise, a second or outer surface 28 faces away from the cavity and encompasses the exterior surfaces of the base and side wall. The inner surface of the side wall is preferably divided by a lip 30 into first and second portions 32, 34. The lip 30 can be optionally provided on the inner surface 26 of the side wall of the dish bottom and acts as a guide for indicating the fill height of the culture media 14. The first portion of the side wall defines an upper rim 36 and the second portion 34 joins the upper rim to the base 22. As illustrated, the base and side wall are shown as a one-piece construction such as a molded arrangement, although other equivalent configurations can be used without departing from the scope and intent of the invention.

Figure 4C:
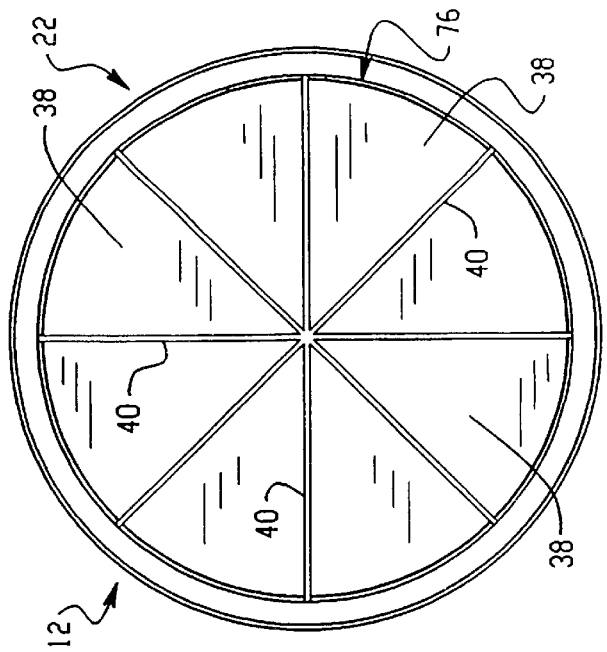
FIG. 4C is a bottom view of the bottom dish.

The dish bottom 12 can be of any convenient dimension, and is usually circular so that this dimension is referenced as a diameter. Typically, the diameter of the dish bottom is about eight (8.0) to fifteen (15.0) cm. The depth of the dish bottom 12 defined by the height of the side wall as it extends upwardly from the base can vary and is generally about 0.8 to 1.8 cm. In certain embodiments (FIG. 4C), the base 22 of the dish bottom 12 can be divided into two, three, four or more sections 38 by sectional dividers, grid markings or other indicia 40 to enhance differential diagnostics of microorganisms (FIG. 4C).

The dish cover or top 16 (FIGS. 1 and 5A–5D) is sized to fit or conform over the dish bottom 12. The dish cover includes a top wall 50, first and second side walls 52, 54, and a seal ring 56. The top wall is disposed at approximately mid-height of the outer side wall 52 for reasons which will be described in greater detail below. In a manner similar to the dish bottom, the side walls 52, 54 are disposed generally orthogonal to the top wall and are themselves radially spaced apart by a gap or recess 58. The side walls are joined along one end by an interconnecting wall 60 to define an inverted, generally J-shaped configuration when the culture dish components are disposed in the first or upright position (FIGS. 1 and 2).

The dish cover has a first or inner surface 70 that generally faces the dish bottom when the individual components of the culture dish are assembled. A second or outer surface 72 extends over the exterior of the dish cover.

The seal ring 56 projects outwardly or downwardly from the inner surface 70 of the top wall 50. The ring is circumferentially continuous and located along the radial periphery of the top wall. It also interconnects along its outer radial edge with the inner or second side wall 54. The seal ring has a planar seal face 78 that cooperates with the culture medium 14 in a dish bottom to define an anaerobic environment for growing microorganisms when disposed in an inverted position (FIG. 3) and as will be described in greater detail below.

The recess 58 in the dish cover is defined between the first and second side walls. When the dish cover 16 is assembled with the dish bottom 12 and placed in an upright position (FIG. 2), the side wall 24 of the dish bottom is received in the recess 58 of the dish cover. The recess can vary in width depending upon the overall size and configuration of the dish cover and dish bottom.

Further, when the cover 16 is joined with the dish bottom 12 and positioned in an upright position, the height of the side wall 52 of the dish cover is sufficient to keep the planar seal face 78 of the seal ring 56 from contacting the medium surface 14. This allows the freshly poured plate with molten agar, to cool and solidify before the media surface of the dish bottom 12 can rest on the seal ring in the dish cover 16 when the assembled culture dish 10 is inverted (FIG. 3). This feature also provides a means for producing finished plates in a continuous manner by mechanized means on a conveyor belt for large scale commercial production while maintaining aseptic conditions.

Figure 3:
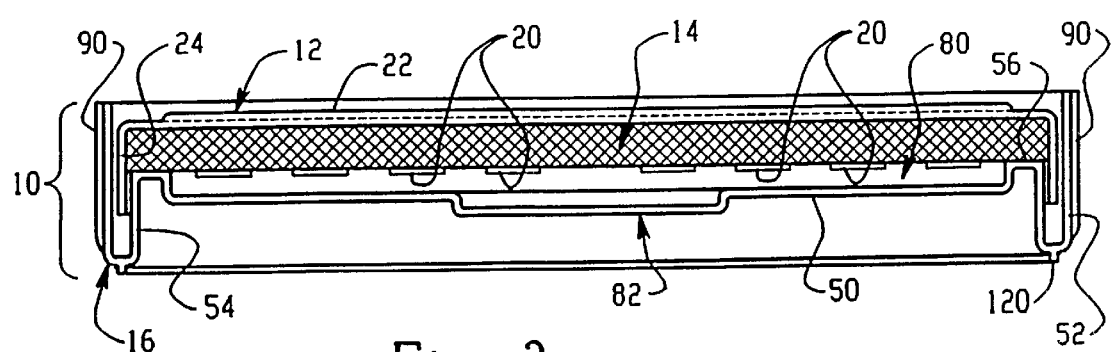
FIG. 3 is a cross-sectional view of the assembled culture dish shown in what is generally referred to as a second or inverted position.
Figure 7:
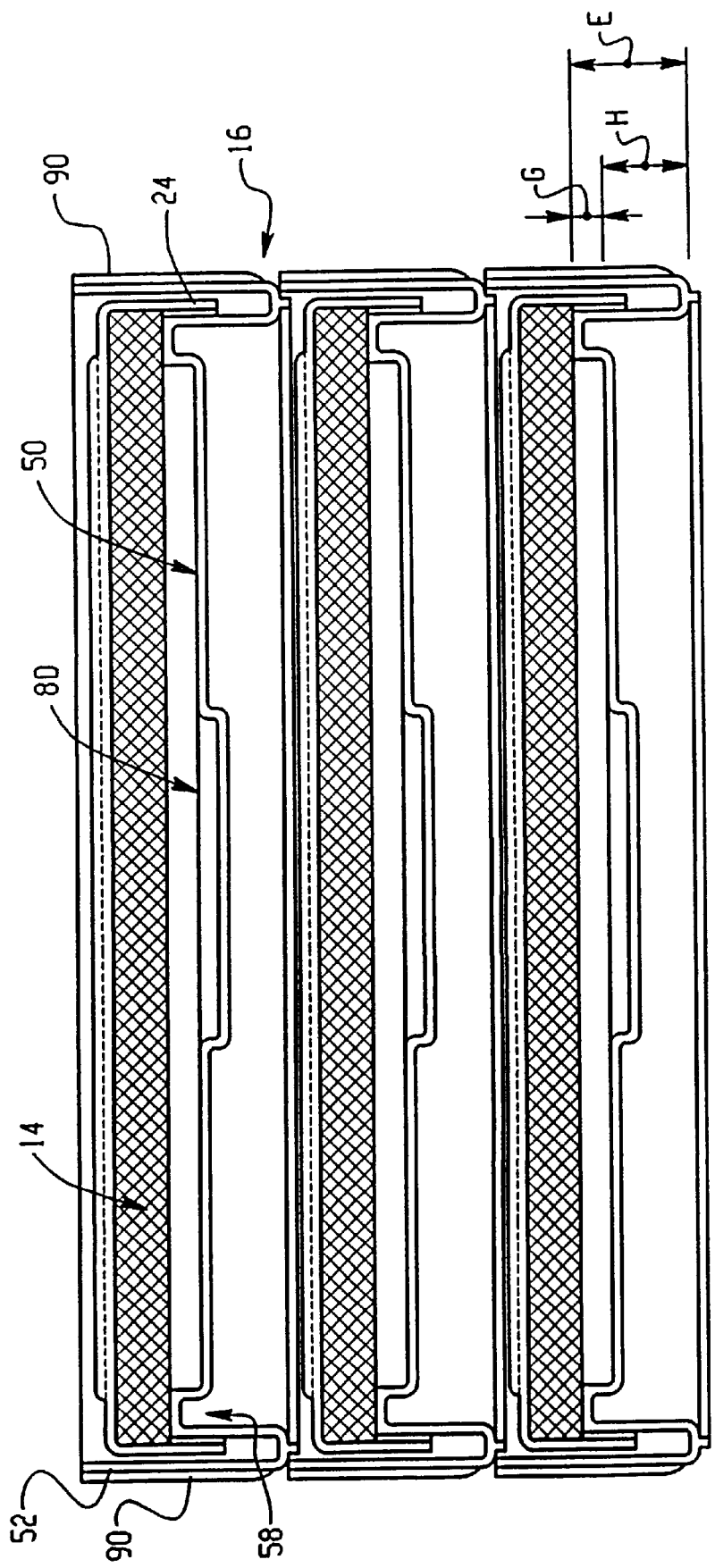
FIG. 7 is a side elevational view of three assembled culture dishes stacked vertically in an inverted position.
Figure 8A:
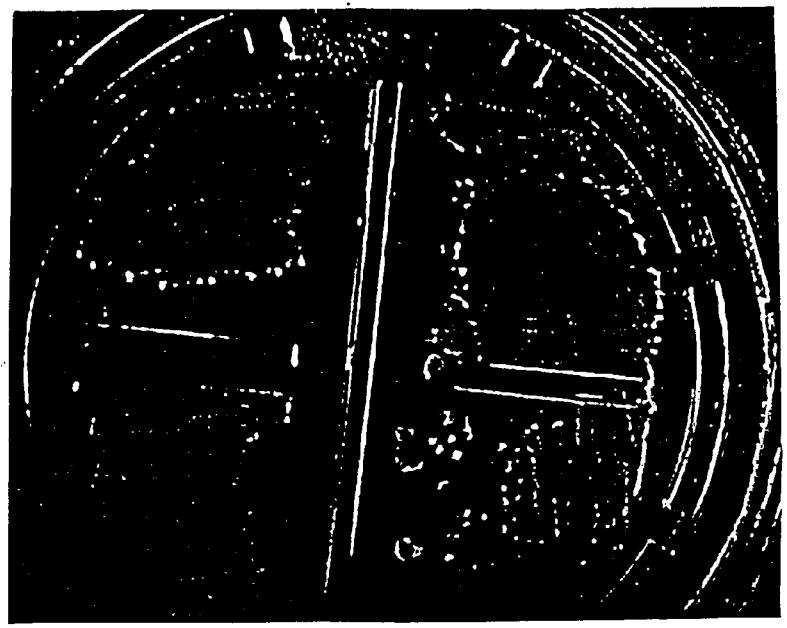
FIGS. 8A and 8B are photographs exhibiting growth of anaerobic organisms in the culture dish of the present invention.
Figure 8B:
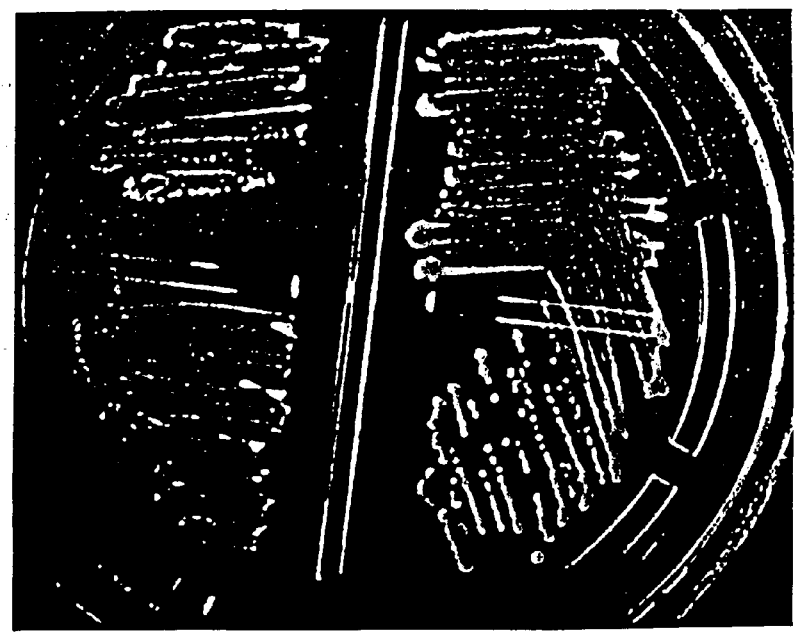

When dish bottom 12 is filled with solidified media 14 and the assembled culture dish 10 is inverted, the solidified media surface will come into contact with the seal ring 56 of the dish cover 16 forming a media-ring seal along the planar seal face 78 (see FIGS. 3 and 7). In this inverted configuration of the culture dish, an oxygen reducing agent present in the media 14 will remove all of the oxygen that is trapped in the head space of the enclosed chamber 80 formed between the surface of the solidified media and the inner surface 70 of dish cover. The assembled culture dish can be incubated aerobically in the inverted position while producing an internal anaerobic environment for the growth of anaerobic microorganisms 20.

In addition, in certain embodiments of the invention, a raised area, dome or cavity 82 is present in the dish cover 16 (FIG. 1). Specifically, projecting outward from the top wall 50 of the dish cover is a dome 82 designed to contain an anaerobic gas ($CO_2$, etc.) generating pad or an indicator strip (not shown). The dome 82 is comprised essentially of a dome side wall 84 and a dome top wall 86, although a circular dome is the more preferred embodiment. It is understood by those skilled in the art that domes or cavities of alternative shapes and sizes can be utilized with equal success.

Figure 6:
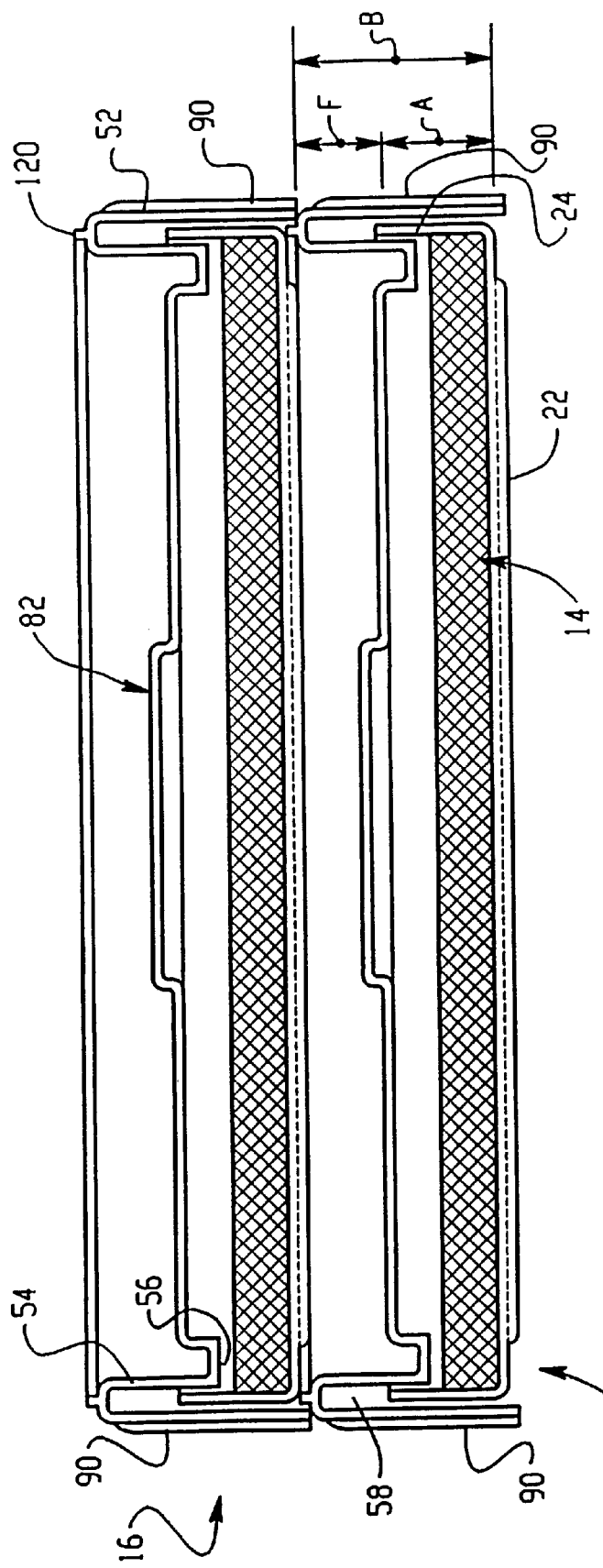
FIG. 6 is a side elevational view of two assembled culture dishes stacked vertically in an upright position.

In accordance with the illustrated embodiment, strengthening ribs 90 are peripherally spaced along side wall 52. The ribs are preferably equally spaced about the circumference of the dish cover and protrude radially outward from the exterior surface of the side wall. The ribs provide additional rigidity and strength to the dish cover which is particularly helpful when the culture dishes are stacked in either the upright or inverted positions as shown in FIGS. 6 and 7.

The dish cover 16 can be of any convenient diameter so long as it mates with the dimensions of the dish bottom 12. Typically, the dish cover 16 is approximately nine (9.0) cm to sixteen (16.0) cm in diameter. The seal ring 56 can be of any desired diameter and is generally about seven (7.0) cm to fourteen (14.0) cm in diameter and is centrally positioned relative to the side wall 52 of the dish cover. The overall radial dimension of the seal ring 56 can vary with a preferred radial dimension being about two-tenths (0.2) cm to one-half (0.5) cm.

Figure 4D:
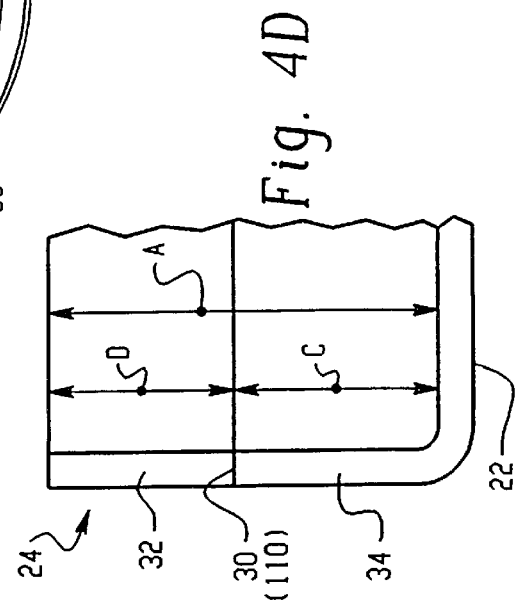
FIG. 4D is an enlarged view of the side wall of the bottom dish.
Figure 4A:
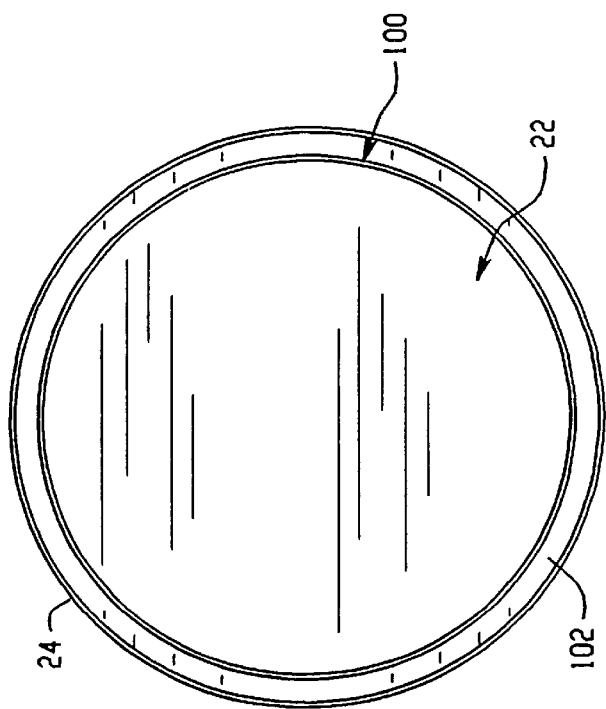
FIGS. 4A is a top view of a first component or bottom dish of the culture dish.
Figure 4B:
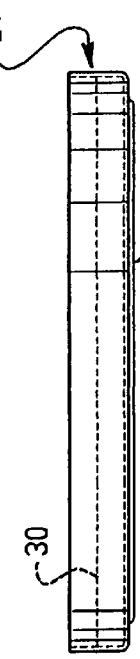
FIG. 4B is a side elevation view of the bottom dish.

Moreover, in some embodiments, the base 22 of the dish bottom 12 contains an indicator ring 100 (FIG. 4A). The area or annulus 102 between the indicator ring 100 of base and the side wall 24 identifies the area on the media surface 14 that the seal ring 56 will occupy when the assembled culture dish 10 is inverted. This area is not to be used for culturing microorganisms. Microbes present in this area will swarm around the seal ring 56 when the dish top is placed in contact with the culture media.

The difference in the height of the side wall 52 of the dish cover in relation to the height of the side wall 24 of the dish bottom can also vary, with a height differential of about one-half (0.5) cm being preferred. The fill height 110 in FIG. 1 and FIG. 4D is the distance from the base 22 of the dish bottom 12 to the surface level of the culture media 14 and is variable. Typically, this height can be two-tenths (0.2) cm to four-tenths (0.4) cm. The dimension from the top of the culture media 14 surface, which is generally indicated by the inner lip 30 to the top edge of the dish bottom is (D) and is determined by the relationship D=A−C. (see FIG. 4D, wherein (A) is the total height of the side wall 24 of the dish bottom 12 and (c) is the fill height of the culture media).

Figure 5A:
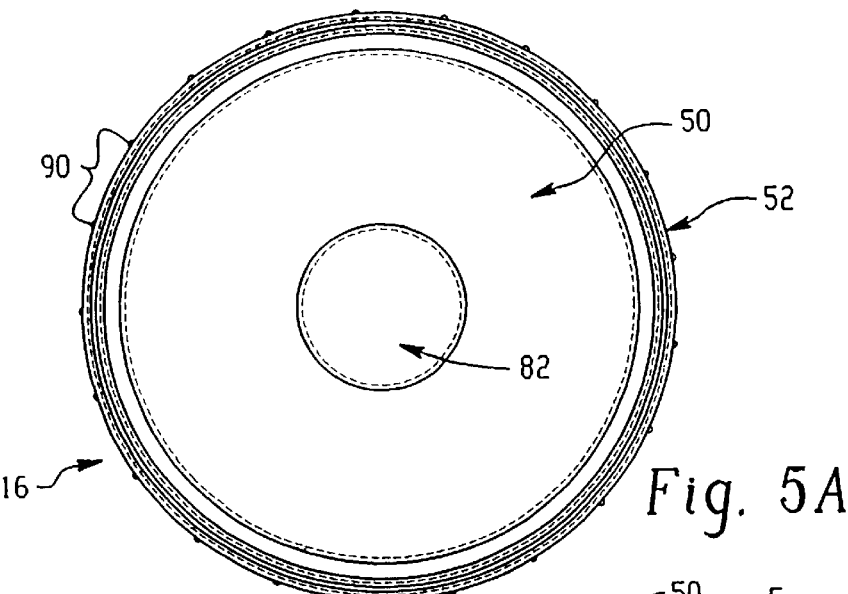
FIGS. 5A is a top view of the second component or dish top or cover of the culture dish.
Figure 5B:
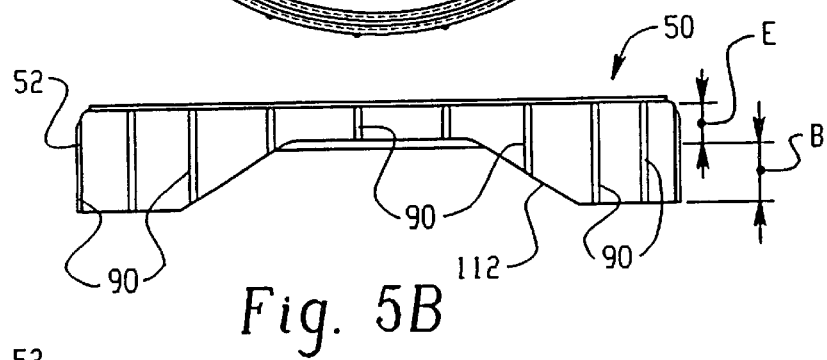
FIG. 5B is a side elevational view of the dish top.
Figures 5C, 5D:
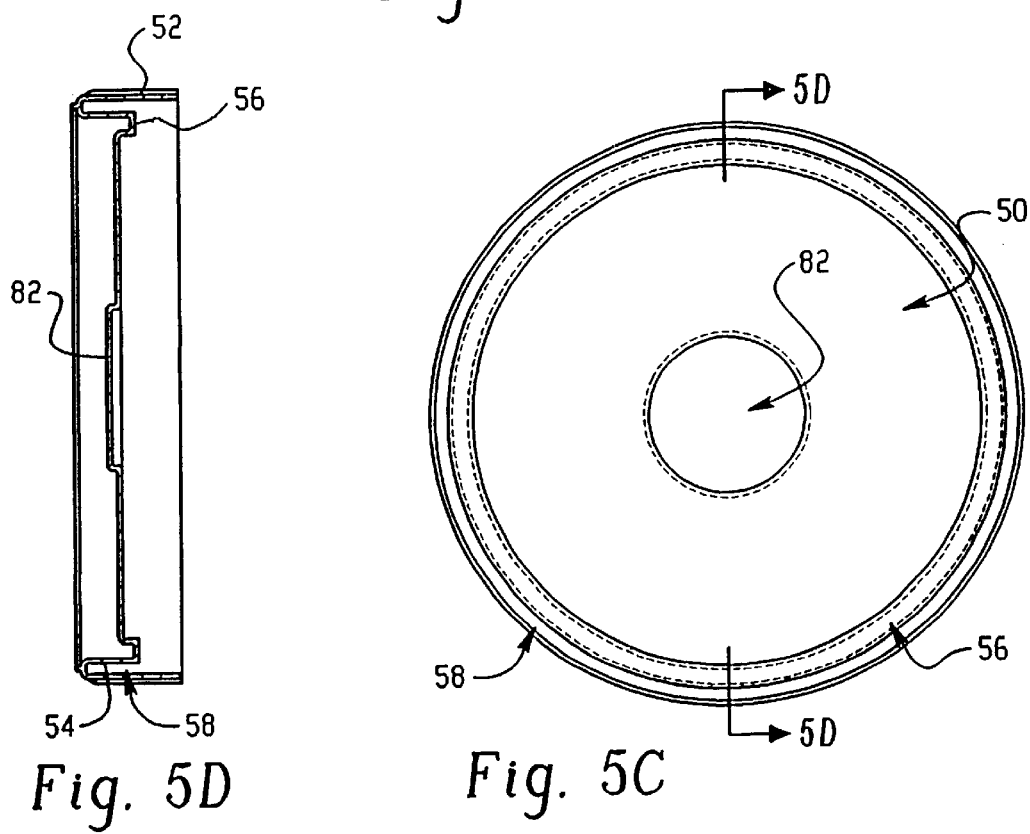
FIG. 5C is a bottom view of the dish top.
FIG. 5D is a sectional view of the dish top taken generally along the lines 5D—5D of FIG. 5C.

The seal ring 56 inside the dish cover extends a distance downward from the dish cover 16 equal to (E) in FIG. 5B which is determined by the relationship E=B −($C_{max}$+0.1 cm), where (B) is the total height of the side wall 52 of the dish cover and ($C_{max}$) is the maximum fill height of the culture media 30. This assures that the seal ring 56 clears the culture medium surface by approximately one-tenth (0.1) cm when the dish bottom 12 is filled to its maximum level and the assembled culture dish 10 is in its upright position (FIG. 2).

The distance between the top edge of the side wall 24 of the dish bottom and the upper extreme of the inner surface 70 of the dish cover 16 when the culture dish is oriented in the upright position is (F) in FIG. 6. In a preferred embodiment, F is determined by F=B−A, where (B) is the total height of the side wall 52 of the dish cover 16 and (A) is the total height of the side wall 24 of the dish bottom 12.

The depth of the headspace or enclosed chamber 80 below the media surface 38 formed when the assembled culture dish is inverted to form a media-ring seal is determined by the dimension (G) in FIG. 7. This dimension can vary depending on the size of the dish top 16, but typically ranges between two-tenths (0.2) cm to one-half (0.5) cm. The dimension (H) in FIG. 7 is the height of the top wall from an upper edge of the dish cover. It is determined according to the following relationship H=E−G, where (E) is the height of the inner side wall 54 of the dish cover and (G) is the height of the headspace 80.

The dish cover preferably includes one or more cut-out areas 112 (FIG. 5B) in a portion of the side wall 52. These cut-out areas 112 facilitate the grasping and separation of the dish bottom 12 from the dish cover in an assembled culture dish 10. The cut-out areas may be variably or constantly spaced from each other in the side wall 52 of the dish cover. As shown, one preferred arrangement has two cut-out areas 112 in the side wall 52 that are equidistant from each other. Likewise, the particular configuration of the cut-out areas may vary without departing from the scope and intent of this invention.

Moreover, in the preferred embodiment of the invention, the assembled culture dishes 10 are designed to be stacked one on top of another. A dish bottom 12 of one assembled culture dish is nestled between stacked dish covers 16 (see FIG. 6) in the upright positions. In this regard, each dish cover has a stacking ring or protruding rib 120 around the upper edge of the dish cover (FIG. 1). While the diameter of the stacking ring 120 can vary, it is generally about one-half (0.5) mm to one (1.0) mm less than the overall peripheral diameter of the dish cover 16. This provides an outer radial ledge 122 upon which the bottom edge of the side wall 52 of an adjacent dish cover rests when placed either in an upright (FIG. 6) or inverted position (FIG. 7). The projection of the stacking ring 120 is preferably about one-half (0.5) mm to one and one-half (1.5) mm in height. The stacking ring 120 prevents an adjacent dish cover from sliding laterally and upsetting the stacked arrangement (see, for example, FIGS. 6 and 7).

Similarly, the stacking ring 120 on the dish cover 16 radially contains or nests an adjacent dish bottom 12 when stacking is desired in an upright position (see FIG. 6). The stacking ring 120 defines a radial inner ledge 124 to impede slide-out of the enjoining dish bottom 12. The stacking ring is preferably one-half (0.5) mm to (1.5) mm in width.

The minimum fill height (Cmin) to which the dish bottom 12 can be filled with culture media 14 and have the media surface rest on the seal ring 56 when the dish is in an inverted position is determined by Cmin=A–E, wherein (A) is the total height of the side wall 24 of the dish bottom 12 and (E) is the height of the inner side wall 54 of the dish cover. If the fill height of the culture media 14 is below this level, then the upper rim of dish bottom 12 rests in contact with the inner surface 70 of the dish cover 16 rather than the media surface 14 resting on the seal ring 56 of the dish cover when the assembled culture dish is inverted. In this situation, there is no seal formed between the seal ring 56 and the medium surface 14. The sealed headspace 80 is not formed. This condition renders the assembled culture dish 10 useless for one designed purpose of the culture dish which is to provide a self-contained environment for the isolation and growth of microaerophiles and anaerobes.

A variant of the culture dish contains one or more perforations or pores 132 in the dish bottom 12 for the purpose of controlling moisture inside the headspace 80. The sizes of the pores 132 can vary but are usually about one-tenth (0.1) cm to three-tenths (0.3) cm in diameter. The number of pores 132 can vary from one (1) to eighty (80) or more and their location can be grouped or evenly spaced. The pores may be covered with an adhesive film (not shown) such as Mylar™ which retards the passage of oxygen and can be sterilized in place when the dish is sterilized. This film can be removed after the culture dish 10 is filled and before it is incubated. The pores provide a means to reduce the water content of the media during incubation in a controlled manner. This reduces the condensate that forms inside the assembled culture dish 10. Any oxygen infiltrating into the assembled culture dish 10 through these pores 132 must pass through the media 14 to get to the media surface where the microbes 20 are planted. The media 14 contains the biocatalytic oxygen reducing agent and optionally one or more substrates that removes the oxygen before it can reach the surface by this route.

The culture dish 10 is designed to be easily manufactured by known injection molding techniques. The dish top 16 and dish bottom 12 have no features that prevent them from being ejected from a mold. The materials of construction can vary but are preferably polystyrene, polycarbonate, or polystyrene-acrylonitrile. These are clear thermoplastics that are inexpensive, easy to mold, sterilizable by ethylene oxide or radiation, resilient to handling and resistant to chemical substances used in microbiological media. Styrene-acrylonitrile has the lowest oxygen permeability of the three thermoplastics mentioned. All of the parts are preferably transparent to permit observation of the anaerobic culturing process. However, pigments or dyes may be added to the polymeric materials in order to produce different shades or colors. Further, as it is understood by those skilled in the art, ultra-violet light absorbers and other additives can be added to produce culture dishes having the properties desired by the end user.

The assembled culture dish 10 can be opened by one of three methods:

A) The assembled and sealed culture dish 10 is placed upright on a bench top. The dome 82 on the dish top 16 is depressed. The flexing of the dish top 16 causes the media-ring seal to part releasing and allowing the dish bottom 12 to come to rest on the bench top.

B) The assembled and sealed culture dish 10 is gently struck onto the bench surface. This action breaks the media-ring seal which in turn releases the dish bottom 12 and allows the dish bottom 12 to come to rest on the bench top.

C) The assembled and sealed culture dish 10 is placed upright on a bench top. The side walls 52 of the dish top 16, between cut-out areas, are gently flexed. This action causes the media-ring seal to part and releases the dish bottom 12 to come to rest on the bench top.

The media-ring seal can be reformed simply by. placing the dish top 16 over dish bottom 12 and. re-inverting the assembled culture dish 10. Gravity will cause the dish bottom 12 containing the solidified media to come into contact with the seal ring. The substrate and/or oxygen reducing agent present in the media 14 will once again remove all of the oxygen trapped in the head space 80.

Figure 10:
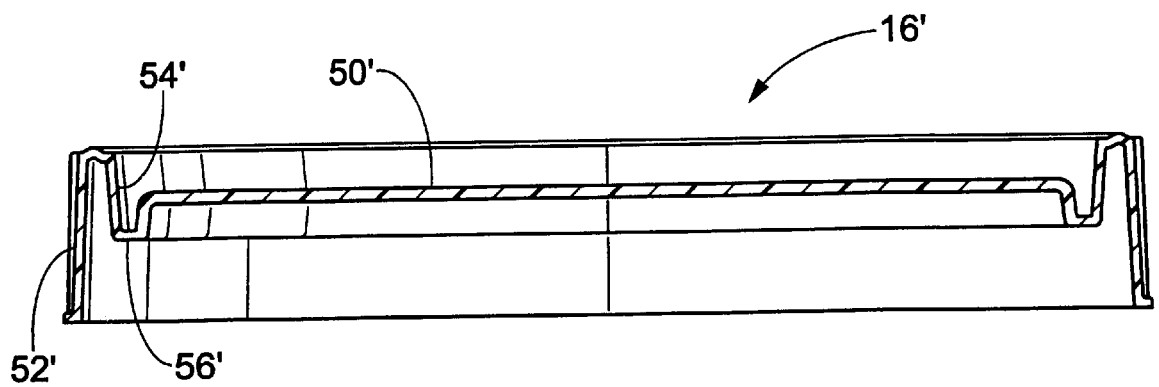
FIG. 10 is a cross-sectional view of another preferred embodiment of a lid or cover of the culture dish assembly.
Figure 9:
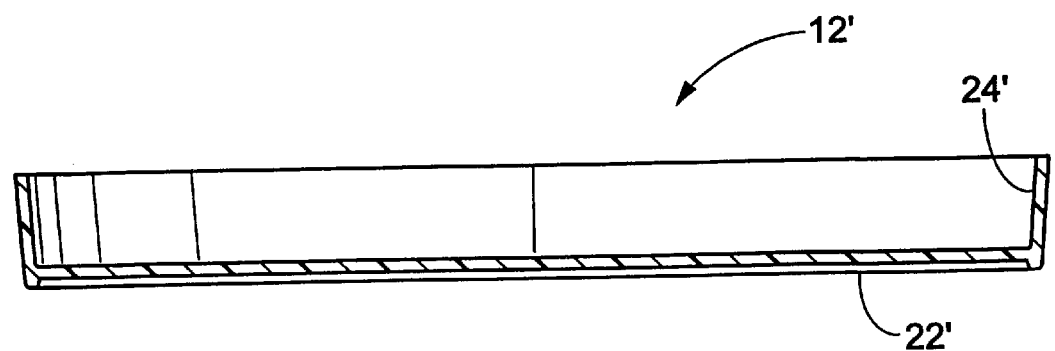
FIG. 9 is a cross-sectional view of another preferred embodiment of a base or bottom dish of the culture dish assembly.
Figure 11:
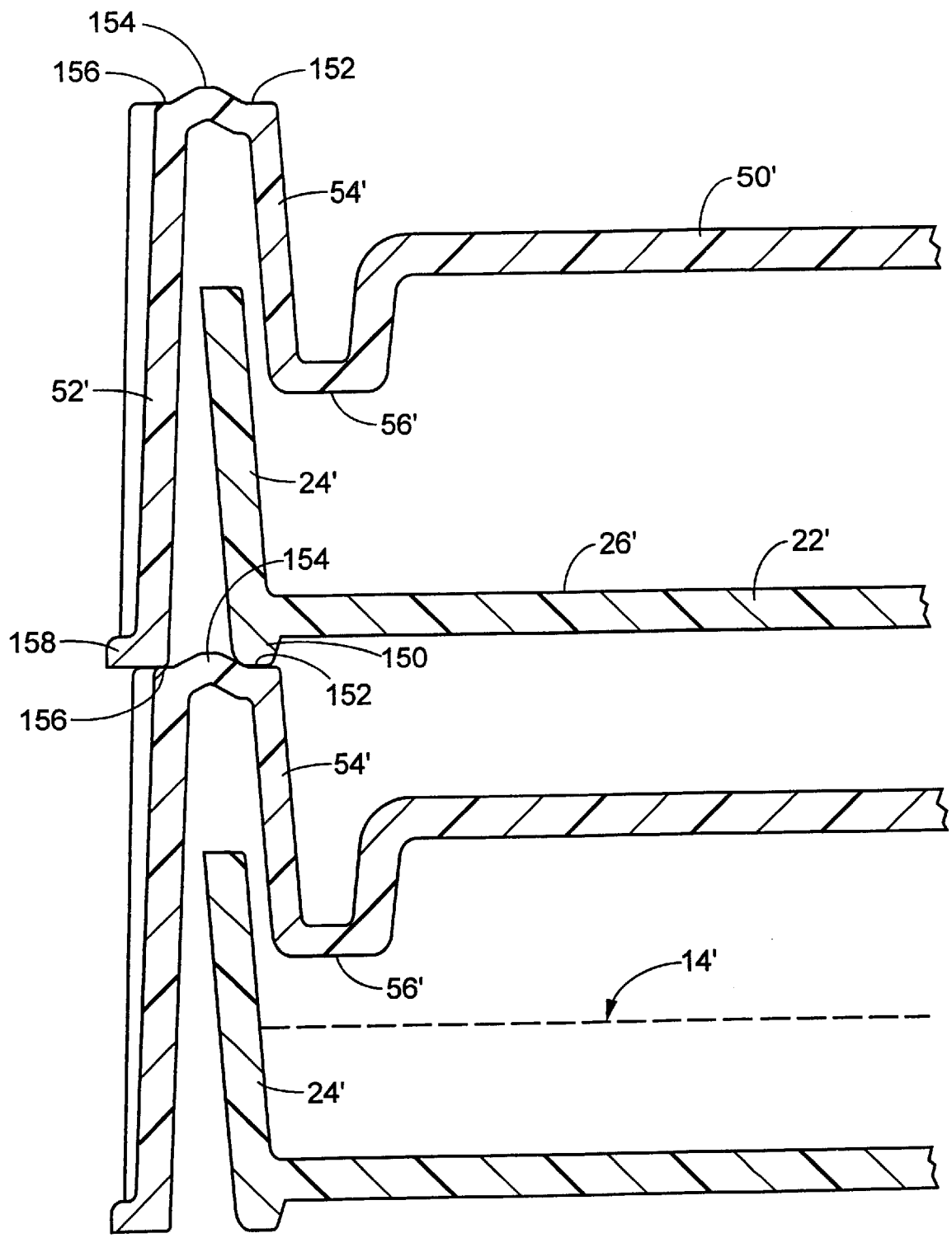
FIG. 11 is an enlarged cross-sectional view of multiple culture dish assemblies stacked in a first orientation.

A second preferred embodiment is illustrated in FIGS. 9–11. Where possible, like numerals will identify like components with a primed suffix, while new components will be identified with a new numeral. Moreover, it will be appreciated that the culture dish assembly of this second preferred embodiment operates in substantially the same manner, i.e., having first and second orientations in which the dish components cooperate with one another.

A first dish or base 12' has a substantially planar wall 22' and a side wall 24' extending therefrom. The side wall has a slight outward taper as it proceeds outwardly from the wall 22'. A culture medium or agar 14' is received in the cup-shaped first dish component (FIG. 11). As described above, the fill height of the culture medium is important so that an effective seal can be achieved between the dish components and the second or inverted orientation. A rib 150 extends outwardly from the generally planar base in a direction generally opposite that of the side wall 24'. In the preferred arrangement, the rib 150 is circumferentially continuous and is radially dimensioned and located to seat on a terminal end of the second leg of the second dish component or lid, as will be described in greater detail below.

The second dish component 16', also referred to as a cover, lid, or top, is sized to fit and conform over the dish bottom. It includes a wall 50' that is substantially planar and first and second side walls 52', 54'. Radially interposed between the planar wall 50' and the second leg 54' is the seal ring 56' defined by a planar, annular seal face. As will be appreciated from a review of FIG. 11, it is apparent that the first and second legs 52', 54' of the lid have tapered conformations. In particular, they define a generally inverted U-shaped configuration. The second leg 54' tapers radially outward from its interconnection with the seal region 56' to an interconnecting portion 152. The interconnecting portion 152 has a radial dimension that supports the rib 150 extending from the first dish. A raised protrusion 154 assists in centering a dish base when disposed in stacked relation on the lid of an adjacent culture dish assembly. Moreover, a support region 156 is disposed radially outward of the protrusion and is adapted to receive the terminal end 158 of the first leg of an adjacent lid. In this manner, assembled dish components in the first orientation can be stacked one atop the other (FIG. 11). The side wall 24' of the base is then received between the diverging first and second legs 52', 54' of the lid. The degree of taper is sufficiently controlled so that region 152 is located for supporting the rib 150 of an adjacent base and region 156 of the interconnecting portion provides suitable support for the first leg of the lid. Moreover, the protrusion 154 serves a centering function to facilitate stacking of the dish components.

In this arrangement, the circumferential side wall defined by the first leg 52' of the lid is also preferably circumferentially continuous. Although the cutouts may facilitate handling of the lid, warpage could occur during the molding operation, thus it will be appreciated that for more precise control of the manufactured component, a circumferentially continuous side wall may be desired in some instances.

Although not illustrated, it will be appreciated that the dish components of the second preferred embodiment also cooperate in the second orientation, or inverted relation in a manner similar to that described above. Thus, the seal face 56' will suitably seat or seal against the surface of the agar 14'. The space between the first and second legs 52', 54' of the lid allows the side wall 24' of the base to move inwardly toward the interconnecting portion between the legs. This movement is stopped by engagement between the seal face and the agar to define a sealed headspace between the culture medium and the generally planar wall 50'.

While the culture dish of the invention has been shown and described herein as being particularly adapted for use in circular form, it is not desired or intended to thus restrict the scope and utility of the improvements by reason of such specific embodiments since the apparatus may be of various shapes and sizes without departing from the invention. In addition, it is also contemplated that certain specific descriptive technology used herein shall be given the broadest possible interpretation consistent with the disclosure.

The biocatalytic oxygen reducing agents suitable for use in the invention include known biocatalytic oxygen reducing agents such as glucose oxidase and catalase and the oxygen scavenging bacterial cell membrane fragments disclosed in U.S. Pat. No. 4,476,224 entitled "Material and Method for Promoting the Growth of Anaerobic Bacteria", issued Oct. 9, 1984 to Howard I. Adler, Oak Ridge, Tenn. one of the co-inventors of the present invention. The '224 patent is incorporated herein by reference.

The '224 patent is directed to a method of removing dissolved oxygen from a nutrient medium for anaerobic bacteria through the use of sterile membrane fragments derived from bacteria having membranes which contain an electron transport system which reduces oxygen to water in the presence of a hydrogen donor in the nutrient medium. It is known that a great number of bacteria have cytoplasmic membranes which contain the electron transport system that effectively reduces oxygen to water if a suitable hydrogen donor is present in the medium. Some of the bacterial sources identified in the '224 patent include *Escherichia coli, Salmonella typhimurium, Gluconobacter oxydans*, and *Pseudomonas aeruginosa*. These bacterial membranes have been highly effective in removing oxygen from media and other aqueous and semi-solid environments.

The same oxygen reducing effects produces by the cell membrane fragments from the bacterial sources indicated above, are also present in the membrane of mitochondrial organelles of a large number of higher non-bacterial organisms. More particularly, a great number of fungi, yeasts, and plants and animals have mitochondria that reduces oxygen to water, if a suitable hydrogen donor is present in the medium. Some of the sources of oxygen reducing membranes from these mitochondria are: beef heart muscle, potato tuber, spinach, Saccharomyces, Neurospora, Aspergillus, Euglena and Chlamydomonas. The process of producing the useful mitochondrial membrane fragments involves the following steps:

1. Yeast, fungal cells, algae and protozoa, having mitochondrial membranes containing an electron transfer system which reduces oxygen to water, are grown under suitable conditions of active aeration and a temperature which is conducive to the growth of the cells, usually about 20° C. to 45° C. in a broth media. Alternately, mitochondria may be obtained from the cells of animal or plant origin.
2. The cells are collected by centrifugation or filtration, and are washed with distilled water.
3. For the preparation of crude mitochondrial membrane fragments, a concentrated suspension of the cells is treated to break up the cell walls and mitochondria. This is accomplished by known means, for example, by ultrasonic treatment or by passing the suspension several times through a French pressure cell at 20,000 psi.
4. The cellular debris is removed by low speed centrifugation or by microfiltration (cross-flow filtration).
5. The supernatant or filtrate is subjected to high speed centrifugation (175,000Xg at 5° C.) or ultrafiltration.
6. For the preparation of material of higher purity, the cells of step 2 are suspended in a buffer containing 1.0 M sucrose and are treated by means which break up the cell walls or membranes but leave the mitochondria intact. This is accomplished by known means, for example, by ultrasonic treatment, passage through a French pressure cell at low pressure, enzymatic digestion or high speed blending with glass beads.
7. The cellular debris from step 6 is removed by differential centrifugation or filtration.
8. The supernatant or retentate from step 7 is passed through a French Press at 20,000 psi to break the mitochondria into small pieces.
9. Mitochondria debris from step 7 is removed by centrifugation at 12,000Xg for approximately 15 minutes or by microfiltration.
10. The supernatant or filtrate from step 9 is subjected to high speed centrifugation (175,000Xg at 5° C.) or ultrafiltration.
11. The pellet or retentate from step 5 (crude mitochondrial fragments) or the pellet or retentate from step 10 (purified mitochondrial membrane fragments) are resuspended in a buffer solution at a pH of about 6.0 to about 8.0. A preferred buffer solution is 0.02 M solution of N-2-hydroxyethylpiperazine-N'-2-ethane sulfonic acid (HEPES).
12. The membrane fragments in the buffer solution are then passed under pressure through a filter having openings of about 0.2 microns.
13. The suspension is then stored at about −20° C. for later use or it may be freeze dried.

Furthermore, while many solidified medium do not require the addition of a hydrogen donor in order for the enzyme system present in the membrane fragments to reduce the oxygen present in the product to water, when synthetic medium or medium failing to contain a hydrogen donating substance are utilized, the addition of a hydrogen donor (i.e., an organic substrate) may be necessary in order for the membrane fragments to perform their oxygen removing functions. Suitable hydrogen donors are lactic acid, succinic acid, alpha-glycerol phosphate, formic acid, malic acid, and where available, their corresponding salts.

The present invention is further illustrated by the following examples. It is to be understood that the present invention is not limited to the examples, and various changes and modifications may be made in the invention without departing from the spirit and scope thereof.

EXAMPLES

Example 1

Growth of Anaerobic Microorganisms using the Culture Dish, i.e., "OxyDish™" of the Present Invention and a Biocatalytic Oxygen Reducing Agent Nutrient agar is supplemented with sodium formate (15 mM), sodium succinate (30 mM), sodium lactate (45 mM) and cysteine (0.025 g/100 ml). A biocatalytic oxygen reducing agent, EC-Oxyrase® (Oxyrase, Inc., Mansfield, Ohio) is added to cooled (45° C. to 50° C.) but molten sterile medium to give a final concentration of 5 units/ml. 20 ml of the above mixture is soon introduced into the bottom part of a culture dish, i.e., "OxyDish™". The top part of the culture dish, is placed over the filled bottom part to prevent contaminants from entering the dish. The agar in the bottom part cools to ambient temperature and solidifies. The covered dish is left standing to permit excess moisture to escape. At this point the dish may be sealed by inverting it to bring the agar surface in the dish bottom into contact with the ring inside the dish top.

A suspension of anaerobic microorganisms is spread on the surface of the agar medium that contains the biocatalytic oxygen reducing agent and its substrates. The dish is sealed by inverting it. The dish is then placed into an aerobic incubator at 35° C. to 37° C. for 24 to 48 hours. Several dishes are stacked to form a stable column of dishes.

Assembled dishes can be handled and viewed at any time without breaching the seal and losing the anaerobic environment inside the trapped headspace. In this way, a particular culture dish, i.e., "OxyDish™" can be selected at the earliest time when the microbial isolate has grown sufficiently for selection.

Using this technique with the culture dish, i.e., "OxyDish™" and a biocatalytic oxygen reducing agent, the following microorganisms have been grown: Clostridium tertium, C. difficile, C. perfringens, C. cadaveris, C. acetobutylicum, Bacteroides thetaiotaomicron, B. fragilis, B. distasonis, Escherichia coli, Fusobacterium varium, F. mortiferum, F. necrophorum, Peptostreptococcus magnus, P. anaerobius, P. nigra, P. intermedius, Lactobacillus casei, L. acidophilus, Eubacterium lentum, Bifidobacterium breve, and Streptococcus fecalis.

Example 2

Measurement of Oxygen Depletion in the Headspace of the Culture Dish Effect of the Present Invention by the Biocatalytic Oxygen Reducing Agent A hole is drilled in the base of the culture dish, i.e., "OxyDish™" and a gas tight septum is inserted. The base is then filled with 20 ml of agar containing a biocatalytic oxygen reducing agent. The bottom is sealed to the top by inverting the assembled dish and incubating it at 37° C. Periodically, 50 ul samples of the gas in the headspace of the dish are sampled by inserting the tip of a 100 ul gas tight Hamilton syringe through the septum in the base of the dish. These samples are introduced into an Oxygen Sensor (IT Corporation) and the concentration of oxygen remaining in the headspace is determined. Using this method it has been determined that all measurable oxygen, less than 10 pp billion, is removed from the head space in two to eight hours depending on the concentration and configuration of the biocatalytic agent used. It has also been determined that the dish can be opened, resealed and, after a suitable incubation period, the head space again becomes anaerobic.

Example 3

Multiple Opening and Closing of the Culture Dish of the Present Invention and Reestablishment of Anaerobic Environment A culture dish, i.e. "OxyDish™" of the present invention containing a nutrient agar and the biocatalytic agent is streaked with an anaerobic organism (Bacteroides thetaiotaomicron or B. fragilis) covering two quadrants of the dish. After 24 hours of incubation at 37° C. the dish is opened, growth of the anaerobe is observed and a small quantity of organism is streaked on the third quadrant of the dish. The dish is resealed and after 24 hours of incubation at 37° C., the dish is reopened and growth is observed in the third quadrant. A small amount of growth from the third quadrant is streaked on the fourth quadrant. The dish is resealed and after a 24 hour incubation at 37° C. it is reopened and growth is observed in the fourth quadrant of the dish.

Example 4

Rapid Anaerobiosis of the Agar Laver Containing a Biocatalytic Oxygen Reducing Agent as Indicated by Methylene Blue An agar medium was made that contained water, 50 mM sodium lactate, and 2.5 mg/ml of methylene blue. In the oxidized state methylene blue is blue in color. In the reduced state it is colorless. The agar was melted and cooled to 45° C. It is blue in color. EC-Oxyrase® is added at 5 units/ml and 20 ml is delivered to the bottom part of a culture dish, i.e., "OxyDish™". As soon as the agar has solidified, about 5 minutes later, the culture dish, i.e., "OxyDish™" is sealed by inverting it. At this time the agar layer is blue in color. The culture dish, i.e., "OxyDish™" is incubated at 37° C. and observed periodically. Soon after sealing the culture dish, i.e., "OxyDish™", the agar layer begins to lighten in color. Within 30 minutes to 45 minutes of being put into the incubator, the medium is nearly white in appearance, but with a light blue tinge of color. By 60 minutes of incubation the agar layer is white, which indicates that the agar layer is anaerobic shortly after the addition of EC-Oxyrase® to the medium.

Example 5

Use of Methylene Blue Strip to Indicate Anaerobiosis in the Culture Dish

A small rectangular piece of filter paper impregnated with methylene blue at an alkaline pH is fixed to the inside of the dome in the top of the culture dish, i.e., "OxyDish™". The dish bottom contains nutrient agar and a biocatalytic oxygen reducing agent. The dish is sealed by inverting it thereby causing the agar surface to rest on the ring. After incubation at 37° C. for 8 hours or more, the blue color disappears from the filter paper. This indicates that the headspace of the culture dish, i.e., "OxyDish™" has become anaerobic.

Example 6

Use of Glucose Oxidase and Catalase as the Biocatalytic Oxygen Reducing Agent

Sterile Nutrient agar (Difco), supplemented with 1% glucose, is cooled to 45° C. and 1 unit of sterile filtered glucose oxidase/ml, and 1 unit of sterile filtered catalase (Sigma Biochemicals, 1994 Catalog, p 221 and p 478) is added. 20 ml of this medium is deliver into a culture dish, i.e., "OxyDish™". After the agar has solidified, a small quantity of *Bacteroides fragilis* is streaked on the surface of the agar and the dish is sealed by inverting it. After 48 hours of incubation at 37° C., growth of the anaerobic microorganisms is observed on the surface of the agar medium.

Example 7

Use of a Filter Pad with Carbonate to Generate $CO_2$ in the Headspace

A piece of filter paper saturated with a 1% sodium bicarbonate solution and then dried is fixed to the inside of the dome in the culture dish, i.e., "OxyDish™" top. This filter paper is then covered by a 0.2 u membrane filter. The dish bottom is filled with 20 ml of Nutrient Agar (Difco) and a biocatalytic oxygen reducing agent, EC-Oxyrase® at 5 units/ml and substrates. The agar surface is inoculated by streaking with a small amount of *Clostridium acetobutylicum*, a microorganism that requires $CO_2$ for rapid colony development. Immediately before sealing the dish, one drop of 0.1 N HCl is placed on the membrane filter. The dish is sealed by inverting it and placed into a 37° C. aerobic incubator. After 24hours of incubation, growth of *C. acetobutylicum* can be observed indicating that $CO_2$ was released from the sodium bicarbonate impregnated filter paper into the headspace of the culture dish, i.e., "OxyDish™".

Example 8

Relief of Moisture Through Pores in the Dish Bottom

Seventy-six holes of different sizes (large: 0.101 inch, medium: 0.086 inch, and small: 0.059 inch) are drilled into a culture dish bottom. The dish is filled with 40 ml of 1.5% agar. A standard dish cover or a Brewer Lid is fitted onto each dish bottom. The complete dish is weighed. The covered dish is incubated at 37° C. and the weighed at timed intervals. The loss of weight is taken as due to the loss of moisture, since the solidified agar is 98.5% water by weight. The relative weight loss, net of control weight loss, is as follows:

| Pore Size | 24 hrs. | 48 hrs. |
|---|---|---|
| Small | 6% | 11% |
| Medium | 9% | 14% |
| Large | 13% | 24% |

This shows that the drying of the agar layer can be controlled during incubation by the number and size of pores put into the dish bottom. For all size holes, the molten agar did not escape through these holes. The Brewer Lid covered dishes exhibited no moisture build up within the trapped headspace for those dishes with holes in them.

Example 9

Comparison of Present Invention With Standard Methods for Growing Anaerobes

The inoculum is prepared by selecting colonies of particular microbes from Wilkens-Chalgren blood agar plates. A loopful of growth is suspended in Brucella broth to a density of about $1.5 \times 10^8$ colony forming units per mL. The suspended microorganisms are put into wells of a replicator block. Sterile replica or pins are dipped into the wells of the block. The replicator pins are stamped onto the surface of agar medium (Wilkens-Chalgren blood agar). Each pin is calibrated to deliver about $1 \times 10^5$ colony forming units per spot. This procedure is repeated to inoculate a controlled pattern of spots onto agar plates containing increasing amounts of antibiotic. Appropriate control plates, that do not contain antibiotics, are included. After a short time, the spots dry, the culture dish, i.e. the OxyDish, is sealed and incubated aerobically. Standard plates, not containing the oxygen reducing agent, i.e. oxyrase®, and substrates, are incubated in anaerobic jars or chambers. After 48 hours of incubation at 35° C. the plates are scored for growth. The presence of growth on a plate containing antibiotic indicates that the particular microbe is resistant to the level of antibiotic in that plate. In this way, one can determine the antibiotic susceptibility profile of a large number of microbial specimens.

With respect to the rate and intensity of growth of a number of difficult anaerobes using the culture dish of the present invention and the brocatalytic oxygen reducing agent compared to the standard methods, it was found that anaerobic microbes grew faster and to a greater density with the present invention compared to standard anaerobic methods. As shown below, this observation was particularly noticeable for difficult to grow anaerobes.

| Microbe | Standard Method | OxyDish Method |
|---|---|---|
| *Clostridium dificil* | 1+ | 3+ |
| *Clostridium perfringens* | 4+ | 4+ |
| *Clostridium cadaveris* | 1+ | 3+ |
| *Bacteroides rhetaiotaomicron* | 3+ | 4+ |
| *Bacteroides distasonis* | 3+ | 4+ |
| *Fusobacterium varium* | 2+ | 4+ |
| *Fusobacterium mortiferum* | 2+ | 4+ |
| *Fusobacterium necrophorum* | 1+ | 3+ |
| *Peptostreptococcus magnus* | 2+ | 3+ |
| *Peptostreptococcus anaerobius* | 1+ | 3+ |
| *Peptostreptococcus negra* | 1+ | 3+ |

| Microbe | Standard Method | OxyDish Method |
| --- | --- | --- |
| *Bifidobacterium breve* | 1+ | 3+ |
| *Prevotella intermedia* | 2+ | 3+ |

The invention has been described with reference to the preferred embodiments. Obviously, modifications and alterations will occur to others upon reading and understanding the preceding detailed description. It is intended that the invention be construed as including all such alterations and modifications insofar as they come within the scope of the claims and the equivalents thereof.

What is claimed is:

1. A culture dish assembly comprising:
   a first dish having a wall and a side wall extending therefrom to define a cavity;
   a second dish having a wall and a side wall extending therefrom that cooperate with the first dish to form a non-sealed assembly in a first orientation of the first and second dishes and a closed headspace in a second, inverted orientation of the first and second dishes.

2. The assembly of claim 1 wherein the wall of the first dish has a substantially circular configuration.

3. The assembly of claim 2 wherein the side wall of the first dish extends outwardly in a substantially perpendicular direction from a periphery of the circular wall.

4. The assembly of claim 3 wherein the side wall of the first dish extends in a first direction from the circular wall.

5. The assembly of claim 1 wherein the wall of the second dish has a substantially circular configuration.

6. The assembly of claim 5 wherein the side wall of the second dish has a generally U-shaped configuration in cross-section defining an annular recess dimensioned to receive at least a portion of the side wall of the first dish therein.

7. The assembly of claim 6 wherein the side wall of the second dish includes first and second legs disposed in generally parallel relation, and the first leg is longer than the second leg and disposed radially outward thereof.

8. The assembly of claim 7 wherein the second dish further includes an annular, circumferentially continuous seal disposed radially inward of the side wall and is disposed in a plane intermediate a terminal end of the first leg and the wall.

9. The assembly of claim 8 wherein the side wall of the first dish has a height less than the first leg of the first dish so that the annular seal is spaced from the wall of the first dish in both the first and second orientations of the first and second dishes.

10. The assembly of claim 8 wherein the side wall of the second dish is circumferentially continuous.

11. The assembly of claim 1 wherein the wall of the first dish is substantially planar.

12. The assembly of claim 1 wherein the wall of the second dish is substantially planar.

13. The assembly of claim 2 wherein the side wall of the first dish tapers radially outward as it extends from the wall.

14. The assembly of claim 5 wherein the side wall of the second dish includes first and second legs defining an annular recess therebetween, the first leg tapering radially outward as it extends substantially perpendicular from the wall.

15. The assembly of claim 14 wherein the second leg tapers radially outward as it extends substantially perpendicular from the wall.

16. The assembly of claim 14 wherein the wall of the first dish includes a rib extending outwardly therefrom and radially dimensioned to seat on a terminal end of the second leg of the second dish.

17. The assembly of claim 16 wherein a terminal end of the side wall of the first dish is dimensioned for radial receipt between the first and second legs of the second dish.

18. The assembly of claim 14 wherein the first and second legs of the second dish are connected by an interconnecting portion having a raised protrusion for locating the wall of the first dish when the first and second dishes are disposed in the first orientation.

19. The assembly of claim 14 wherein the first and second legs of the second dish are connected by an interconnecting portion that has a radial dimension adapted to support the wall of a first dish and a terminal end of a second leg of an adjacent second dish in a first orientation of the dishes.

20. The assembly of claim 19 wherein the interconnection portion includes a raised protrusion separating regions on which the wall of a first dish and a terminal end of a second leg of an adjacent second dish are supported in a first orientation of the dishes.

21. A culture dish assembly comprising:
    a first dish having a base and a vertically raised, peripheral wall extending therefrom to define a cavity for retaining a culture medium therein;
    a second dish having a peripheral groove and an annular sealing ring disposed radially inward of the peripheral groove;
    the peripheral groove sized to receive said vertically raised wall when the first and second dished are placed in aligned facing relation to form said assembly;
    the sealing ring spaced apart from the culture medium when the assembly is in a first orientation and the sealing ring engaging the culture medium when the assembly is in a second orientation which is inverted relative to the first orientation.

22. A culture dish assembly comprising:
    a first dish having a wall and a side wall extending therefrom to define a cavity;
    a second dish having a wall and a side wall extending therefrom that cooperate with the first dish to form a non-sealed assembly in a first arrangement of the first and second dishes, and a closed headspace in a second arrangement of the first and second dishes, the second arrangement being inverted with respect to the first arrangement.

* * * * *